(12) United States Patent
Nogre et al.

(10) Patent No.: US 9,320,779 B2
(45) Date of Patent: Apr. 26, 2016

(54) PROCESS FOR SEPARATING PROTEINS FIBRINOGEN, FACTOR XIII AND BIOLOGICAL GLUE FROM A SOLUBILIZED PLASMA FRACTION AND FOR PREPARING LYOPHILISED CONCENTRATES OF SAID PROTEINS

(71) Applicants: Michel Nogre, Vanves (FR); Pierre Porte, Prunay sur Essonne (FR); Michel Tellier, Eaubonne (FR)

(72) Inventors: Michel Nogre, Vanves (FR); Pierre Porte, Prunay sur Essonne (FR); Michel Tellier, Eaubonne (FR)

(73) Assignee: LABORATOIRE FRANCAIS DU FRACTIONNEMENT ET DES BIOTECHNOLOGIES, Les Ulis (FR)

( * ) Notice: Subject to any disclaimer, the term of this patent is extended or adjusted under 35 U.S.C. 154(b) by 61 days.

(21) Appl. No.: 14/056,903

(22) Filed: Oct. 17, 2013

(65) Prior Publication Data

US 2014/0154231 A1    Jun. 5, 2014

Related U.S. Application Data

(62) Division of application No. 11/477,212, filed on Jun. 28, 2006, now Pat. No. 8,598,319.

(30) Foreign Application Priority Data

Jun. 29, 2005    (FR) ...................... 05 06640

(51) Int. Cl.
| | | |
|---|---|---|
| *C12N 9/10* | (2006.01) | |
| *C07K 14/75* | (2006.01) | |
| *A61K 38/45* | (2006.01) | |

(52) U.S. Cl.
CPC ............... *A61K 38/45* (2013.01); *C07K 14/75* (2013.01); *C12N 9/1044* (2013.01)

(58) Field of Classification Search
CPC .......................... C07K 14/75; C12N 9/1044
See application file for complete search history.

(56) References Cited

U.S. PATENT DOCUMENTS

| 4,377,572 A | 3/1983 | Schwarz et al. |
|---|---|---|
| 5,099,003 A | 3/1992 | Kotitschke et al. |
| 5,206,140 A | 4/1993 | Marder et al. |
| 5,252,709 A | 10/1993 | Burnouf et al. |
| 5,612,456 A | 3/1997 | Bishop et al. |
| 5,834,420 A | 11/1998 | Laub et al. |
| 5,981,254 A | 11/1999 | Bui-Khac |
| 6,121,232 A | 9/2000 | Nur et al. |
| 6,960,463 B2 | 11/2005 | Kanellos et al. |
| 7,241,603 B2 | 7/2007 | Seelich et al. |
| 7,276,235 B2 | 10/2007 | Metzner et al. |
| 7,795,399 B2 | 9/2010 | Eibl |
| 2003/0069399 A1 | 4/2003 | Takahashi et al. |
| 2003/0232969 A1 | 12/2003 | Lengsfeld et al. |
| 2005/0197493 A1 | 9/2005 | Metzner et al. |
| 2006/0009376 A1 | 1/2006 | Eibl |
| 2007/0161122 A1 | 7/2007 | Boulange et al. |

FOREIGN PATENT DOCUMENTS

| EP | 0131740 A2 | 1/1985 |
|---|---|---|
| EP | 0305243 A1 | 3/1989 |
| EP | 0359593 A1 | 3/1990 |
| EP | 0555135 A1 | 8/1993 |
| EP | 0771234 A1 | 5/1997 |
| EP | 1151007 A1 | 11/2001 |
| EP | 1161958 A1 | 12/2001 |
| EP | 1259262 A1 | 11/2002 |
| EP | 1457497 A1 | 9/2004 |
| EP | 1527786 A1 | 5/2005 |
| GB | 2041942 A | 9/1980 |
| JP | H11503125 A | 3/1999 |
| JP | 2003055257 A | 2/2003 |
| JP | 2004057029 A | 2/2004 |
| WO | WO 9303147 A1 | 2/1993 |
| WO | WO 9525748 A1 | 9/1995 |
| WO | WO 9602571 A | 2/1996 |
| WO | WO 9617631 A1 | 6/1996 |
| WO | WO 9923111 A1 | 5/1999 |
| WO | WO 9937680 A1 | 7/1999 |
| WO | WO 0145719 A1 | 6/2001 |
| WO | WO 0148016 A1 | 7/2001 |
| WO | WO 2004007533 A1 | 1/2004 |
| WO | WO 2008113589 A1 | 9/2008 |

OTHER PUBLICATIONS

Cohn, E.J. et al., Preparation and properties of serum and plasma proteins. IV. A system for the separation into fractions of the protein and llpoprtein components of biological tissues and fluids, J. Am. Chem. Soc, Mar. 1946, vol. 68, pp. 459-475.
Kistler, P. et al., "Large scaleproduction of human plasma fractions. Eight years experience with the alcohol fractionatiion procedure of Nitschmann, Kistler and Lergier," Vox Sang., 1962, vol. 7 pp. 414-424.
Siebenlist, K.R., et al., 1996 Biochemistry 35: 10448-10453.
Siebenlist, Kevin R., et al., "Plasma factor XIII binds specifically to fibrogen molecules containing Y chains," Biochemistry, 1996, vol. 35, pp. 10448-10453.
Sober, H.A. et al., 1958 Federation Proceedings 17: 1116-1126.
Tao, Sun et al., "Isolation of human fibrinogen by axial and radial flow chromotograph from Nitschmann fraction 1" Biotechnology Techniques, 1999, vol. 13 pp. 831-835.

*Primary Examiner* — Marsha Tsay
(74) *Attorney, Agent, or Firm* — Birch, Stewart, Kolasch & Birch, LLP

(57) ABSTRACT

Process for separating proteins fibrinogen, Factor XIII and biological glue from a solubilized plasma fraction and for preparing lyophilized concentrates of said proteins.

13 Claims, No Drawings

PROCESS FOR SEPARATING PROTEINS FIBRINOGEN, FACTOR XIII AND BIOLOGICAL GLUE FROM A SOLUBILIZED PLASMA FRACTION AND FOR PREPARING LYOPHILISED CONCENTRATES OF SAID PROTEINS

This application is a Divisional Application of copending application Ser. No. 11/477,212 filed on Jun. 28, 2006, which claims priority to Application No. 05 06640 filed in France on Jun. 29, 2005. The entire contents of all of the above applications are hereby incorporated by reference for all purposes.

FIELD OF THE INVENTION

The present invention is related to a process for separating proteins fibrinogen, Factor XIII and biological glue, and for preparing highly purified lyophilised concentrates of said proteins, and is also related to said lyophilised concentrates capable to be obtained by the process.

BACKGROUND OF THE INVENTION

Fibrinogen is an essential protein for the blood coagulation because its polymerisation to insoluble fibrin, which is formed at the end of the reaction cascade governing the coagulation, leads to the formation of a clot, blocking the vascular gap, responsible for the bleeding. The formation of the clot is essential to stop the bleeding. Further, the fibrin formed on the wound level forms a fibrillary network ensuring the tissue repair (wound healing).

Congenital fibrinogen deficiencies can lead to serious diseases. In order to treat these deficiencies, it is necessary that fibrinogen concentrates, which can be administered to patients under treatment, are available. Other pathologies can also be treated by administering of fibrinogen, especially in cases of massive blood losses (surgery, traumas, etc.), or following to a disseminated intravascular coagulation syndrome (CIVD).

Moreover, biological glues, activated by thrombin, containing fibrinogen as the major component, and Factor XIII (FXIII), are efficiently used in tissue repair in clinics, such as skin transplantation, nervous and arterial sutures, as described, for example, in patents EP 0 305 213, FR 2 448 900 and FR 2 448 901. The presence of Factor XIII or transglutaminase in these products contributes to the stabilization of fibrin by formation of intercatenary covalent, bindings which make it insoluble. In some cases, these products are obtained by means of rather complex fibrinogen production processes, which require an external supply of purified Factor XIII, in order to be able to perform their therapeutic function.

Therefore, production of fibrinogen, biological glues and Factor XIII concentrates, especially for therapeutic uses, requires purification techniques leading to these products, which are not only sufficiently free of various contaminants, such as the accompanying or co-precipitated proteins, antibodies or proteases but, in addition, their viral safety is increased.

The isolation of fractions enriched in fibrinogen, possibly containing FXIII, from plasma, is well known and first described by Cohn and Nitschmann (Cohn et al, J. Am. Chem. Soc., 68, 459, 1946 and Kistler et al, Vox Sang., 7, 1962, 414-124). More recent methods combine precipitating techniques of different plasma sources with filtration, chromatography, viral, inactivation techniques, etc. The following patents and patent applications can be cited as examples: EP 0 359 593, U.S. Pat. No. 5,099,003, EP 0 305 243, FR 2 448 900 and FR 2 448 901.

Nevertheless, different processes yielding concentrates or compositions either of fibrinogen, as described in the patent application EP 1 457 497, or of biological glue, for example according to the patent EP 0 771 324, or enriched in fibrinogen containing further associated proteins such as FXIII, Factor VIII, fibronectin, Factor von Willebrand etc. (especially U.S. Pat. No. 6,121,232) are carried out.

These processes, however, involve the use of separate production lines consequently using different methods employing several sources of raw materials for obtaining these considered proteins. Furthermore, depending upon the case, these methods can involve expensive chromatographic substrates, such as affinity gels based on chelated metals (WO 2004/007533) liable to release residual metals into the eluate, which can lead to unwanted reactions with the proteins (for example oxidation). This creates problems of clumsiness of the carrying out on industrial scale, when these three purified active principles are needed together. These problems are even more obvious when the different thus obtained proteins are to be subjected to a viral inactivation and/or viral and other unwanted contaminants, such as prions, removal treatment.

To this end, some classical viral inactivation treatments implementing a heat treatment, such as pasteurisation at 60° C., for 20 hours, in the presence of protecting stabilizers, and a chemical treatment, such as solvent-detergent, intended to make the above concentrates compatible with therapeutic use, do not allow to inactivate completely the viruses, especially non-enveloped viruses (parvovirus B19, hepatitis A and B, etc.).

In order to find a solution to this drawback, use is currently made of more efficient viral inactivation processes, such as dry heat treatment under harsh conditions (80° C., 72 h). This step requires the incorporation of a suitable stabilizing formulation offering conditions such as, for example, the fibrinogen stabilization in this step, while the viruses are being destroyed. Such a formulation is the subject-matter of a patent application FR 04 02001 filed by the Applicant. However, this formulation can be applied to the stabilization of a defined protein and not of the accompanying proteins, characteristics of which are different of those of fibrinogen.

The filtration techniques, especially the nanofiltration using filters with a porosity of 35 nm, and even less, have also been carried out in order to remove viruses. However, this technique cannot be efficiently used without controlling the physical and chemical parameters influencing the recovery output of compounds to be filtered, and this by avoiding the clogging of the filter and the passage of various viruses and contaminants. These parameters, such as ionic strength, pH of the solution, and filtration process conditions, as well, lay down the specific process conditions which depend also on the nature of the compound(s) contained in the solution to be filtered. Although the patent applications EP 1 348 445 A1, EP 1 161 958 A1 and WO 99/23111 disclose the nearly total removal of very small sized non-enveloped viruses present in the protein solutions, such as hepatitis A, by nanofiltration, making use of filters of 15 nm, however, the risk of transmission of unwanted viruses or prions is always present.

In order to avoid this risk, a double or even a triple viral inactivation and/or removal combining at least two of the above mentioned techniques can be performed, as described for example in the patent application WO 2004/007533. When such treatments are combined, then it is essential to choose, depending upon the viral inactivation method, the virucidal excipients and/or protecting stabilizers which are not exerting a concomitant deleterious effect, as for example on the above mentioned physical and chemical parameters governing the nanofiltration.

SUMMARY OF THE INVENTION

Therefore, the Applicant investigated the development of a process for separating fibrinogen, Factor XIII and biological glue activated by thrombin meeting a double objective. On one hand, the development of a unique process which allows to obtain together concentrates of these freeze-dried and highly purified proteins from a single plasmatic raw material containing fibrinogen and Factor XIII, and, on the other hand, this process should be compatible with at least one viral inactivation and/or viral and other unwanted contaminants (polymers, aggregates, prion) removal treatment, as well.

Therefore, the present invention is related to a process for separating proteins fibrinogen, Factor XIII and biological glue from a solubilized plasma fraction, based on fibrinogen and Factor XIII, and for preparing freeze-dried concentrates of said proteins comprising the following steps of:
  a) as chromatographic purification comprising the steps of: loading an anion exchanger of weak base type with the said solubilized fraction, said exchanger being previously equilibrated with a buffer having a predetermined ionic strength of an alkaline pH, thus allowing the retention of the biological glue,
    elution of the biological glue by increasing of the ionic strength of the said buffer,
  a) separation of FXIII from fibrinogen by addition to at least a part of the biological glue eluate of at least one chemical agent precipitating the FXIII, and recovery of the resulting supernatant solution of purified fibrinogen, and
  b) diafiltration of the fibrinogen, biological glue and resolubilized FXIII solutions, followed by a freeze-drying of said solutions.

Thus, the Applicant found that freeze-dried, highly purified, fibrinogen, Factor XIII and biological glue concentrates, free of coprecipitated proteins and of unwanted contaminants, can be obtained on industrial scale by means of a unique flexible process which allows, depending upon the needs, to adjust optimally the production of each considered compound, while ensuring the optimal profitability of the raw material. Such a simple, rapid and low cost process is easy to carry out on industrial scale, and yields an increased optimisation of various production flow-charts.

Moreover, depending upon the used raw material and the intended application, additional process steps of viral inactivation and/or removal are yielding the three concentrates of interest, suitable for therapeutic use.

The invention is related to a process for separating proteins fibrinogen, Factor XIII and biological glue from a solubilized plasma fraction and for preparing freeze-dried concentrates of said proteins comprising the steps of:
  chromatographic purification comprising the steps of loading an anion exchanger of weak base type with the said solubilized fraction, previously equilibrated with a buffer of a predetermined ionic strength of an alkaline pH, which allows to retain the biological glue, elution of the biological glue by increasing the ionic strength of the said buffer, and
  separation of FXIII from fibrinogen by addition to at least one part of the biological glue eluate of at least one chemical agent precipitating the FXIII, and recovery of the resulting purified fibrinogen containing supernatant solution, and
  diafiltration of the fibrinogen, biological glue and resolubilized FXIII solutions, followed by a freeze-drying of said solutions. It is also related to freeze-dried concentrates of the said proteins capable to be obtained by carrying out the process.

DETAILED DESCRIPTION OF THE PREFERRED EMBODIMENTS

According to the invention, use can be made of several sources of raw materials containing fibrinogen and Factor XIII. Thus, these plasma fractions are obtained by plasma fractionation collected under conditions which are unfavourable for maintaining a sufficient ratio of Factor VIII, which is a labile protein, following to the Cohn process using cold alcohol. It is also possible to apply the above mentioned fractionation to a previously solubilized cryoprecipitate, as far as the extraction of Factor VIII is not aimed, for example in the case of a cryopreciptate with an expired shelf-life or not meeting the conformity requirements of the minimal content of Factor VIII, or to cryoprecipitate depleted plasma. So these different sources of fibrinogen constitute a precipitate of Cohn fraction I which, after washing, is dissolved in any suitable buffer with a neutral pH, known by those skilled in the art. For example, such a buffer is based on sodium chloride, trisodium citrate and L-arginine, with a pH of about 7.4, containing each component in a concentration preferably of 0.12 M, 0.01 M and 0.05 M, respectively.

Thus the flexibility of the process of the invention is also related to the variety of raw materials liable to contain extractible fibrinogen, the purification of which yields the three considered concentrates intended for targeted therapeutic uses.

The process can also include, prior to step a), an initial prepurification step of the solubilized plasma fraction by a classical pretreatment with aluminium hydroxide and/or by a precipitation at low temperature. The addition of aluminium hydroxide ensures the removal of unwanted proteins, such as the Factors II (FII), VII, IX and X (FX). This prepurified fraction can be frozen until being used in order to carry out the following process steps of the invention.

The chromatographic purification of the solubilized plasma fraction is carried out on any matrix based on a natural or synthetic polymer, resin or gel, on which are grafted groups of anion exchangers of weak base type, such as the DEAE. Classical chromatographic substrates of this type are available under trade names DEAE-Sepharose® CL-6B, DEAE-Trisacryl LS, Fractogel TSK-DEAE 650 M or F, DEAE-Macroprep (Bio-Rad, France), etc.

The equilibrating buffer of the anion exchanger presents a predetermined ionic strength and its pH value has to be in the alkaline range.

The equilibrating buffer has an ionic strength typically of less than 0.2 and, preferably, is in the range of values of from 0.06 to 0.2. More particularly, the ionic strength is in the range of values of from 0.08 to 0.15. It is preferably adjusted by addition of inorganic salts of alkali or alkali-earth metals or mixtures thereof, most preferably of inorganic salts of alkali metals, particularly of sodium chloride.

The maximal pH value of the equilibrating buffer is such as to avoid any denaturation of the considered products, that is of about 10. Advantageously, the pH is in the range of values higher than 7 up to 9, preferably from 7.5 to 8.2. By way of example, this buffer contains a concentration of 0.06 M of sodium chloride with a pH of 7.9-8.1, and very preferably can further comprise trisodium citrate in a preferred concentration of 0.011 M. Any other buffer based on sodium chloride or on inorganic salts of alkaline or earth-alkaline metals, comprising further biologically active compounds, which are compatible and not denaturating the products of interest, can also be used.

When the above solution has been applied to the anion exchanger, the biological glue is retained on the substrate. The process can include, prior to the biological glue elution step, a washing step with the said equilibrating buffer of the anion exchanger until not retained proteins and contaminants are removed. This washing step allows, by percolation of this buffer on the substrate, the passage into the filtrate of the not-retained or weakly retained, on the exchanger, proteins present in the solution containing the fibrinogen, such as immunoglobulins G (IgG), A (IgA) and M (IgM) and albumin, and contaminants, such as the chemical viral inactivation agents. The washing period of time is determined by measuring the optical density (OD) of the filtrate at a wavelength of 280 nm. Indeed, a value of OD corresponding to that of the baseline is a good indication that the above mentioned compounds were effectively eliminated.

After return to the baseline, the elution of the biological glue is carried out by increase of the ionic strength of the equilibrating or washing buffer, the pH of which is preferably set to a value of 7.4-7.6. The value of this ionic strength is selected with the aim of obtaining an efficient elution of the biological glue, making sure that this value does not alter the properties of the considered product. Advantageously, the value of the ionic strength is in the range between 0.5 and 1.3, particularly between 0.9 and 1.1. This increase of the ionic strength is carried out by addition of any here above defined salt or mixture of salts, especially of sodium chloride. Moreover, the elution buffer can contain further excipients, such as a mixture of components called mixture A, comprising trisodium citrate (10 to 12 g/l), lysine (1 to 5 g/l), glycine (1 to 5 g/l), Tris salt (2 to 5 g/l), arginine (25 à 50 g/l) and isoleucine (5 à 15 g/l). The protein concentration in the eluate is of about 4 g/l.

At least one part of the recovered amount of the biological glue eluate is subjected to a treatment in order to separate the FXIII accompanying the fibrinogen. This separation is carried out by precipitating of the FXIII by addition, to the eluate to be treated, of a chemical precipitating agent, which can be present in form of an aqueous solution in a concentration allowing to attain the desired effect. Preference is given to aqueous solutions based on citrate salts 1 M, as for example sodium citrate and, especially, trisodium citrate. Thus, a precipitate of FXIII and a supernatant highly enriched in fibrinogen are separated. A very efficient recovery of the FXIII precipitate can be achieved by filtration on filters of 5 µm.

The so recovered FXIII precipitate is resolubilized, preferably in water or in a buffer. In particular, it is dissolved in a buffer of mixture A, the pH of which is in the range of 6.9-7.1, so that its concentration corresponds to an activity of about 100 times higher than that of normal plasma. As such, the FXIII precipitate can be for example solubilized in a way that its concentration be of about 1 to 5 g of total protein.

According to the invention, solutions of biological glue (biological glue eluate) and of fibrinogen (supernatant enriched in fibrinogen) can be concentrated by ultrafiltration, up to contents typically between 15 and 25 g of total protein/l determined by classical measuring methods well known to those skilled in the art.

The three obtained fibrinogen, Factor XIII and biological glue solutions, optionally concentrated, are subjected to a diafiltration step. This step is intended at first to remove the possible excess, on one hand, of the inorganic salt used for obtaining solutions with an ionic strength as high as 0.2 M, and, on the other hand, of the precipitating agent present in the resolubilized precipitate. It should be noted that the presence of important amounts of inorganic salt, necessary for eluting the biological glue, may have a deleterious effect on the efficiency of the freeze-drying process and also on the viral inactivation by dry heating, and on the virus retention ability of a suitable nanofilter. This step can also be necessary in order to incorporate, if need be, suitable excipients, stabilizers and protecting agents, which should allow, on one hand, the dry heating of fibrinogen, of FXIII and of biological glue, avoiding the risk of denaturation, and, on the other hand, the rapid solubilization of the freeze-dried products, typically in a period of time of 3 to 8 min. The preferred diafiltration buffer contains the mixture A, and has a pH in the range of 6.9-7.1, in reference to the patent application FR 04 02001 filed by the Applicant.

It should be noted that an other advantage of the invention is that, according to other preferred embodiments of the process, the diafiltration buffer comprising the mixture A can already be present as a component of the biological glue elution buffer. Thus the carrying out of the diafiltration happens to be simplified and optimised.

Diafiltration buffers of different composition can also be used, depending upon the needs, provided that they meet the above mentioned requirements.

The here above mentioned ultrafiltration step can also be carried out under the same conditions at this stage of the process.

The respective solutions, optionally diafiltrated, optionally concentrated, are freeze-dried by means of classical methods and under current conditions, that is at a temperature in the range between −40° C. and −30° C., for about 48 hours.

Moreover, the process can include at least one step of viral inactivation and/or viral and the abovementioned contaminants, such as prions, removal treatment. This treatment can be selected from the group consisting of the chemical viral inactivation treatment, the nanofiltration and the dry heat viral inactivation treatment.

Thus, this step can be carried out by a classical chemical viral inactivation treatment, preferably consisting of a solvent-detergent treatment, according to the method described in the patent EP 0 131 740. Preferably, the viral inactivating chemical agents are a mixture of Tween®-TnBP, more preferably, the mixture of Triton (octoxinol)-TnBP, typical concentrations of which are of 0.3% (v/v) and 1% (p/v) respectively. This viral inactivation can be integrated at any stage of the process, but it can be carried out judiciously prior to the step a) of the chromatographic purification step. So it will contribute to an efficient removal of the inactivating agents.

In a preferred embodiment of the process, a nanofiltration step can also be provided for, in order to remove the viruses, especially non-enveloped viruses and other exogenous contaminants, completing the previous chemical viral inactivation treatment. Filters of 35 nm can be efficiently used, although other nanometric filters can be used as far as the filtration periods of time and the efficiency of viral retention are optimised. The nanofiltration is carried out with the eluate obtained in step a) or, if the case arises, with the diafiltrated fibrinogen, biological glue and resolubilized FXIII solutions, prior to freeze-drying. The judicious choice of chemical parameters of the chromatographic purification, and those of the diafiltration allows a flexibility of the carrying out of nanofiltration without modifying its performances.

Finally, the dry heat viral inactivation treatment can be carried out on the freeze-dried products fibrinogen, biological glue and FXIII under classical conditions, at 80° C., for 72 hours, in order to inactivate the non-enveloped viruses, which would not have been inactivated and/or removed in at least one of the previous viral inactivation and/or removal steps.

Further, the dry heated freeze-dried products can be reconstituted in an aqueous medium suitable for clinical use, preferably in purified water for injection (PPI), and used directly for intravenous injection.

Moreover, the process of the invention can comprise at least one step of clarifying filtration in order to remove insoluble particles, and at least one sterilizing step, these being carried out in a current way using filters, for example, of 0.8 to 0.1 μm. Particularly, they are related to the solubilized prepurified plasma fraction, the eluate of biological glue obtained in the step b) and/or the diafiltrated solutions of the three compounds of interest.

Thus, the carrying out of the process yields freeze-dried, highly purified biological glue and fibrinogen concentrates which have a respective content of fibrinogen, compared to the content of total proteins, of about 90%. Further, the Factor XIII activities in the biological glue and fibrinogen concentrates are respectively of about 5 U/ml and of about 1.5 U/ml.

The obtained Factor XIII concentrate is free of contaminating proteins, and presents an activity, if need be, in the range of values of about 30 U/ml to about 700 U/ml, preferably of 100 U/ml to 400 U/ml, depending upon the concentration obtained by resolubilization of the FXIII precipitate and/or after ultrafiltration.

The invention is also related to freeze-dried fibrinogen, biological glue and Factor XIII concentrates, obtainable by performing the above process, characterized in that they comprise the mixture of diafiltration buffer components (mixture A). Furthermore, the said concentrates can be of therapeutic quality thanks to the integration of at least one step of viral inactivation and/or viral and contaminants removal treatment, selected from the group consisting of the chemical viral inactivation treatment, the nanofiltration and the dry heat viral inactivation treatment, into the process of the invention.

The following Example illustrates one embodiment of the present invention without limiting its scope.

Example 1200 l of human cryoprecipitate-depleted plasma are used. This plasma is subjected to a precipitation with ethanol according to Cohn's method, under the conditions known by those skilled in the art, in such a way that the considered ethanol concentration in the plasma is of 8% (v/v) and the temperature of the obtained mixture is of −3° C.

Further, the thus obtained supernatant and precipitate are subjected to a centrifugation. 10 kg of precipitate are obtained, which is the impure Cohn fraction I.

The impure Cohn fraction I (10 kg) is suspended and washed with 300 l of buffer <<Blombach>>, comprising a mixture of glycine 1 M, of trisodium citrate 0.055 M and of ethanol 6.5% (v/v), at a pH of 6.8.

After centrifugation, 8 kg of purified precipitate paste (purified Cohn fraction I) are recovered then dissolved at a temperature of 37° C., in 60 l of buffer constituted of a mixture of sodium chloride 0.12 M, of trisodium citrate 0.010 M and of arginine 0.05 M, pH 7.4.

The thus obtained precipitate solution is then subjected to a pre-purification treatment with alumina gel, at a ratio of 108 g per 1 kg of precipitate paste, at a temperature of 25° C., and a pH of 6.9-7.1.

As soon as the prepurification treatment is achieved, the solution is subjected to lenticular clarifying filtrations by means of cellulosic fibres filters (Seitz, type K700) of 0.65 μm and to sterile filtrations with filters of 0.2 μm.

This prepurified solution is subjected to a first viral inactivation treatment by solvent-detergent in presence of Tween®-TnBP, of concentrations respectively of 0.3% (v/v) and 1% (p/v), according to the method described in EP 0 131 740.

The thus treated prepurified solution is diluted to 50% by addition of the required volume of an aqueous trisodium citrate 0.010 M solution.

The thus obtained prepurified solution contains furthermore, besides the fibrinogen and the accompanying Factor XIII, unwanted proteins, such as immunoglobulins G and albumin, and contaminants, such as Tween®-TnBP. The efficient removal thereof is carried out by means of a chromatographic step.

To this end, the prepurified solution is injected onto a chromatographic column filled with an anion exchanger gel DEAE Macroprep (Bio-Rad, France) previously equilibrated with a buffer constituted of sodium chloride 0.06 M and trisodium citrate 0.011 M, adjusted to a pH 8.0 M, with an osmolarity of 130-150 mosmolkg$^{-1}$. Under these conditions, fibrinogen and Factor XIII, constituting the biological glue, are retained on the substrate. The weakly retained or not retained proteins on the substrate are removed into the filtrate, and Tween® and TnBP as well, by several subsequent washings with the same buffer.

When the DO, measured at 280 nm, falls back to the baseline, the elution of fibrinogen and Factor XIII, constituting the biological glue, is carried out by means of an elution buffer containing sodium chloride 1M and a mixture A' constituted of trisodium citrate (11.2 g/l), lysine (2.0 g/l), glycine (2.0 g/l), Tris salt (2.40 g/l), arginine (40 g/l) and isoleucine (10 g/l), the ph adjusted to 7.5, with an osmolarity>2000 mosmolkg$^{-1}$.

The thus recovered purified biological glue eluate is treated by nanofiltration on PLANOVA filters (Asahi, Japan) of 35 nm, with a surface of 1 in order to remove the viruses which would have not been inactivated by the previous solvent-detergent treatment. The total protein content, at this stage of the process, is of about 4.0 g/l of solution.

50% of volume of the biological glue eluate are isolated and a solution of trisodium citrate 1M is added to the remaining volume of eluate in order to precipitate the Factor XIII. After making sure that the entire amount of Factor XIII was precipitated, isolation and recovery by filtration on Sartopure filters (Sartorius France) of 5 μm were carried out.

The thus recovered FXIII precipitate is solubilized in purified water for injection, with a ratio of about 1 g/l.

The biological glue (eluate) and fibrinogen solutions are concentrated by ultrafiltration on Biomax Millipore filters 100 kDa with a surface of 5 m$^2$ in a way that the protein content of each solution attains 15 g/l.

The concentrated here above solutions and the solution of FXIII are subjected to a diafiltration on the same filters then those used for the diafiltration against the here above defined mixture A', with a pH 6.9-7.1, an osmolarity of 590-610 mosmolkg$^{-1}$, allowing to remove the sodium chloride, as well.

After carrying out a sterile filtration on 0.45-0.2 μm filters, 100 ml of each diafiltrated solution were taken and were put into glass vials in order to carry out a freeze-drying at a temperature between −40° C. and −30° C. for about 48 hours.

The obtained freeze-dried fibrinogen, biological glue and Factor XIII are subjected to an ultimate step of viral inactivation by dry heating at 80° C. for 72 hours, and stocked before being used in therapy.

The results of quality controls performed on 3 consecutive batches are shown in the following Table.

| Proteins | FXIII[a] | Biological glue | Fibrinogen |
|---|---|---|---|
| Yield (%) | — | 87 ± 3 | 93 ± 4 |
| FXIII:Ag (U/ml) | 31.1 ± 2.1 | 9.3 ± 0.4 | 2.6 ± 0.9 |
| Activity of FXIII (U/ml) | 33.3 ± 1.5 | 5.2 ± 0.4 | 1.3 ± 0.6 |
| Fibronectin (mg/ml) | 0.16 ± 0.03 | 1.10 ± 0.04 | 1.10 ± 0.02 |
| IgM (μg/ml) | 35 ± 0.4 | 209 ± 46 | 183 ± 31 |
| IgG (μg/ml) | 6 ± 2 | 29 ± 6 | 29 ± 5 |
| IgA (μg/ml) | <12 ± 3 | 55 ± 2 | 40 ± 4 |
| FII:Ag | 3 ± 0.2 (μg/l) | 1.9 ± 0.6 (mU/ml) | 1.2 ± 0.2 (mU/ml) |
| Activity of FX (mU/ml) | — | <1.3 ± 0.04 | <1.3 ± 0.03 |
| Plasminogen (μg/ml) | — | 73 ± 4 | 73 ± 7 |

[a]total protein concentration of 1.2 g/l

The invention claimed is:

1. A freeze-dried biological glue concentrate, obtained by a process comprising the steps of:
   i) equilibrating an anion exchanger of weak base type with a first buffer having a predetermined ionic strength of an alkaline pH,
   ii) loading said anion exchanger of weak base type with a Cohn fraction I, thus allowing the retention of the biological glue,
   iii) eluting the biological glue with a second buffer having an alkaline pH and an ionic strength greater than said first buffer,
   iv) concentrating the biological glue by ultrafiltration, and
   v) diafiltering the biological glue solution, followed by freeze-drying of said solution, wherein said concentrate contains a mixture from 10 to 12 g/l of trisodium citrate, from 1 to 5 g/l of lysine, from 1 to 5 g/l of glycine, from 2 to 5 g/l of Tris, from 25 to 50 g/l of arginine and from 5 to 15 g/l of isoleucine.

2. A freeze-dried Factor XIII (FXIII) concentrate, obtained by a process comprising the steps of:
   i) equilibrating an anion exchanger of weak base type with a first buffer having a predetermined ionic strength of an alkaline pH,
   ii) loading said anion exchanger of weak base type with a Cohn fraction I, thus allowing the retention of the biological glue,
   iii) eluting the biological glue with a second buffer having an alkaline pH and an ionic strength greater than said first buffer,
   iv) concentrating the biological glue by ultrafiltration, and
   v) separating FXII from fibrinogen by adding to at least a part of the biological glue eluate at least one chemical agent precipitating the FXIII, wherein the chemical agent precipitating the FXIII is present in the form of an aqueous solution based on sodium citrate and resolubilizing the precipitated FXIII, and
   vi) diafiltering the resolubilized FXIII solution, followed by freeze-drying said solution, wherein said concentrate contains a mixture from 10 to 12 g/l of trisodium citrate, from 1 to 5 g/l of lysine, from 1 to 5 g/l of glycine, from 2 to 5 g/l of Tris, from 25 to 50 g/l of arginine and from 5 to 15 g/l of isoleucine.

3. The freeze-dried concentrate according to claim 1 or 2, wherein said first buffer has an ionic strength of less than 0.2.

4. The freeze-dried concentrate according to claim 1 or 2, wherein the pH of said first buffer is in the range of values higher than 7 up to 9.

5. The freeze-dried concentrate according to claim 1 or 2, wherein the process includes, prior to the biological glue elution step, a washing step with said first buffer of the anion exchanger until not retained proteins and contaminants are removed.

6. The freeze-dried concentrate according to claim 1 or 2, wherein the biological glue elution is carried out with said second buffer having an ionic strength in a range between 0.5 and 1.3, the pH of which is set to a value of 7.4-7.6.

7. The freeze-dried concentrate according to claim 1 or 2, wherein the chemical agent precipitating the FXIII is present in the form of an aqueous solution based on citrate salts 1 M.

8. The freeze-dried concentrate according to claim 1 or 2, wherein the diafiltration is carried out against the buffer containing a mixture of trisodium citrate, lysine, glycine, arginine and isoleucine.

9. The freeze-dried concentrate according to claim 1 or 2, the process by which the concentrate is obtained further comprising at least one step of viral inactivation and/or viral and contaminants removal treatment, selected from the group consisting of a chemical viral inactivation treatment, a nanofiltration and a dry heat viral inactivation treatment.

10. The freeze-dried concentrate according to claim 1 or 2, wherein the nanofiltration is carried out with the eluate obtained in step a) or with the diafiltered fibrinogen, biological glue and resolubilized FXIII solutions, prior to freeze-drying.

11. The freeze-dried concentrate according to claim 1 or 2, wherein a concentration step by ultrafiltration is carried out prior to the step of diafiltration or following the said step, prior to freeze-drying.

12. The freeze-dried concentrate according to claim 1 or 2, including, prior to step a), an initial prepurification step of the solubilized plasma fraction by a classical pretreatment with aluminium hydroxide and/or by a precipitation at low temperature.

13. The freeze-dried concentrate according to claim 1 or 2 of therapeutic quality, obtained by carrying out of a process including at least one step of viral inactivation and/or viral and contaminants removal treatment, selected from the group consisting of a chemical viral inactivation treatment, a nanofiltration and a dry heat viral inactivation treatment.

* * * * *